(12) United States Patent
Almarri et al.

(10) Patent No.: US 11,977,041 B2
(45) Date of Patent: May 7, 2024

(54) SMART JET FUEL AND DIESEL CONDUCTIVITY ANALYZER

(71) Applicant: Saudi Arabian Oil Company, Dhahran (SA)

(72) Inventors: Khaled F. Almarri, Dhahran (SA); Hassan M. Alzain, Dammam (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/385,145

(22) Filed: Jul. 26, 2021

(65) Prior Publication Data

US 2023/0029733 A1 Feb. 2, 2023

(51) Int. Cl.
| | |
|---|---|
| *G01N 27/06* | (2006.01) |
| *G01F 23/00* | (2022.01) |
| *G01N 1/14* | (2006.01) |
| *G01N 33/28* | (2006.01) |
| *G01R 31/382* | (2019.01) |

(52) U.S. Cl.
CPC .............. *G01N 27/06* (2013.01); *G01N 1/14* (2013.01); *G01N 33/28* (2013.01); *G01F 23/00* (2013.01); *G01R 31/382* (2019.01)

(58) Field of Classification Search
CPC .......... G01N 27/06; G01N 1/14; G01N 33/28; G01F 23/00
See application file for complete search history.

(56) References Cited

U.S. PATENT DOCUMENTS

| | | | |
|---|---|---|---|
| 6,899,580 B1 | 5/2005 | Kollmann | |
| 2010/0006284 A1* | 1/2010 | Sonne | E21B 49/081 166/264 |
| 2015/0103089 A1 | 4/2015 | Sogo | |
| 2015/0122488 A1* | 5/2015 | Hodgson | E21B 47/113 166/250.01 |
| 2015/0316527 A1* | 11/2015 | Stock | G01N 23/223 73/54.16 |
| 2016/0047792 A1* | 2/2016 | Ghosh | G01N 25/00 73/61.46 |
| 2016/0103089 A1* | 4/2016 | Boyette | G01N 21/645 356/72 |
| 2017/0176368 A1* | 6/2017 | Pennington | G01N 27/06 |
| 2017/0328856 A1* | 11/2017 | Banks | G01N 27/403 |
| 2020/0003599 A1* | 1/2020 | Theuveny | G01N 33/2823 |

(Continued)

OTHER PUBLICATIONS

"D-2 Incorporated JF-1A-RC RampCheck Product Brochure," D2 Inc., Part No. JF-1A-RC, Revision Date Sep. 11, 2015, Drawing No. 450-001R6, Product Brochure, URL <d-2inc.com/wp-content/uploads/2015/09/450-001-R6-RampCheck-Brochure.pdf>, available on or before May 19, 2021, Sep. 11, 2015, 6 pages.

(Continued)

*Primary Examiner* — Farhana A Hoque
*Assistant Examiner* — Dilara Sultana
(74) *Attorney, Agent, or Firm* — Fish & Richardson P.C.

(57) ABSTRACT

Systems, methods, and a machine readable medium for measuring conductivity in a hydrocarbon sample are provided. An example conductivity analyzer includes a peristaltic pump to flow the hydrocarbons over a temperature controller and a conductivity probe. The temperature controller includes a Peltier block. The conductivity analyzer also includes the conductivity probe.

24 Claims, 4 Drawing Sheets

(56) References Cited

U.S. PATENT DOCUMENTS

2020/0369536 A1* 11/2020 Motkuri .................. A62D 3/40

OTHER PUBLICATIONS

"JF-1A-HH Handheld Conductivity Sensor," SETA Stanhope, Conductivity Measurement of Aviation Fuels, ASTM D2624; IP 274; DEF STAN 91-91, ASTM D1655; ISO 6297, Product Brochure, URL <www.stanhope-seta.co.uk/wp-content/uploads/99708-0_Handheld_Conductivity.pdf>, available on or before May 19, 2021, 4 pages.

"Standard Test Methods for Electrical Conductivity of Aviation and Distillate Fuels," ASTM D2624-15, ASTM International, West Conshohocken, PA, 2015, 11 pages.

SAIP Examination Report in Saudi Arabian Appln. No. 122431396, dated Sep. 27, 2023, 14 pages, with English Translation.

* cited by examiner

SMART JET FUEL AND DIESEL CONDUCTIVITY ANALYZER

TECHNICAL FIELD

The present disclosure is directed to a system and method for determining conductivity of a hydrocarbon at a designated temperature.

BACKGROUND

The conductivity of hydrocarbons, such as jet fuel and gasoline, is an important parameter for quality control. If the conductivity is too low, pumping the fuel may cause a build-up of static electricity, potentially providing an ignition source during fueling operations. For example, an acceptable range for the conductivity for jet fuel is between about 50 pS/m (picoSiemens per meter) and about 600 pS/m.

Conductivity may be measured by standard techniques, such as ASTM D2624-15, Standard Test Methods for Electrical Conductivity of Aviation and Distillate Fuels, ASTM International, West Conshohocken, PA, 2015, which describes the use of portable conductivity meters. However, conductivity is affected by temperature. Portable conductivity meters often use temperature measurements to correct conductivity measurements.

SUMMARY

An embodiment described in examples herein provides a conductivity analyzer for hydrocarbons. The conductivity analyzer includes a peristaltic pump to flow the hydrocarbons over a temperature controller and a conductivity probe. The temperature controller includes a Peltier block. The conductivity analyzer also includes the conductivity probe.

Another embodiment described in examples herein provides a method for using a conductivity analyzer for hydrocarbons. The method includes operating a peristaltic pump to circulate hydrocarbons over a heatsink coupled to a Peltier block and over a conductivity probe, adjusting a temperature of the hydrocarbons to a temperature setpoint, and measuring a conductivity of the hydrocarbons while adjusting the temperature.

Another embodiment described in examples herein provides a machine-readable medium. The machine-readable medium includes instructions that, when executed by a processor direct the processor to perform a conductivity measurement cycle on a hydrocarbon fluid using an analyzer.

DETAILED DESCRIPTION

Embodiments described in examples herein provide a system and method for measuring electrical conductivity at a fixed temperature. Jet fuel is pumped at a temperature other than the temperature it was certified at the source or the distribution bulk plant. As such, the customer may receive a fuel with a significantly different conductivity reading. Similarly, the introduction of ultra-low sulfur diesel in Saudi Arabia is also a critical area of application for this invention, especially when ultra-low sulfur diesel is co-batched with jet fuel. The invention is a handheld lightweight device that includes an integral Peltier effect conductor block with reversible polarity electronics; this is to allow for sample temperature selection. In addition, a peristaltic pump is included to allow for fluid circulation within the sample flow cell and Peltier-block surface. The sample flow cell contains an electrode capable of producing measurements compliant with ASTM D-2624. An appropriately sized lithium-ion battery powers the invention.

The instrument and technique described in examples herein solves the problem of different conductivity readings at different temperatures. As fuel moves through distribution systems, its certified conductivity is relied upon as a quality control parameter. However, fuel is often certified at different temperatures than at the distribution location, or at the point of use, such as an aircraft wing. This can result in noncompliant conductivity readings due to measurement at different temperatures, or to the overuse of fuel conductivity enhancers to ensure fuel remains compliant throughout the supply chain. Another problem of concern is the introduction of ultra-low sulfur diesel fuel in certain countries such as Saudi Arabia. Ultra-low sulfur diesel fuel must be dosed with conductivity enhancers and the dosage for diesel fuel is extremely low, and temperature effects can cause relatively large reading deviations between sources, such as refineries, tanker ships, trucks, and destinations, such as bulk plants, tank farms, and point of sales.

Figure 1:
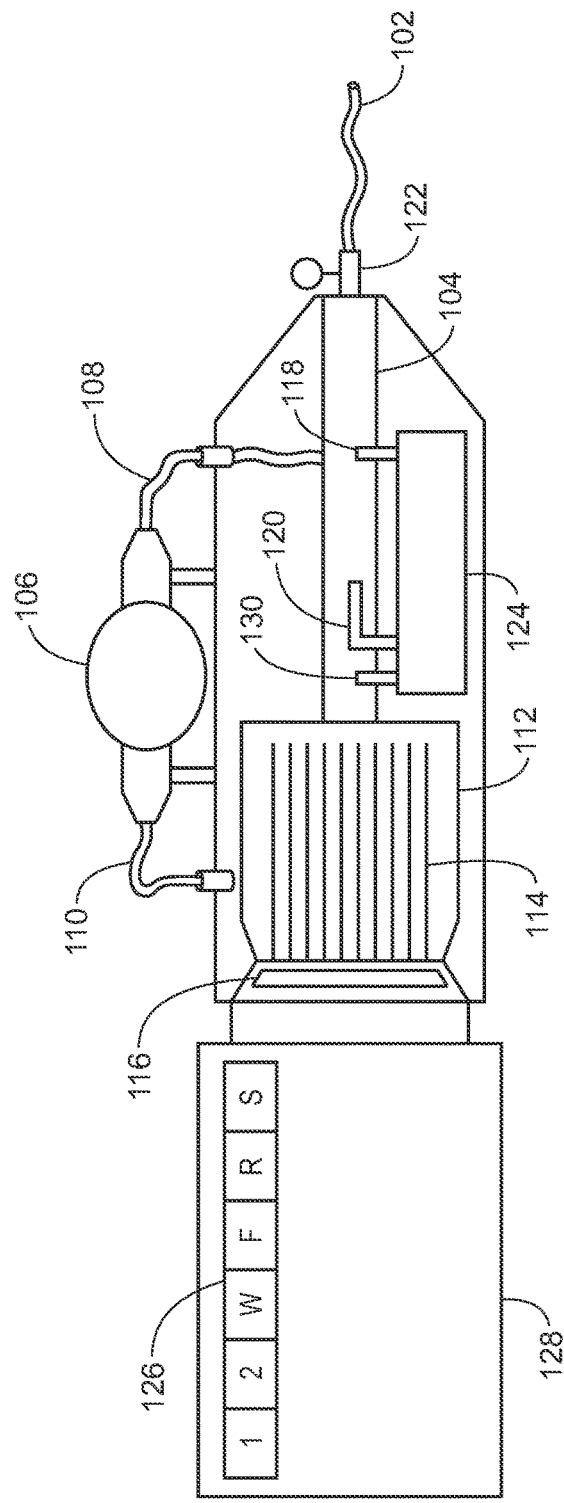
FIG. 1 is a drawing of a smart jet fuel and diesel conductivity analyzer with integrated sample temperature control.

FIG. 1 is a drawing of a smart jet fuel and diesel conductivity analyzer (the analyzer) 100 with integrated sample temperature control. A sampling tube 102 is used to pull a hydrocarbon sample into the sample chamber 104 using a peristaltic pump 106. The peristaltic pump can be a commercially available unit, such as a digital peristaltic pump model DFR0523 available from DFROBOT of Shanghai, China, among others.

The peristaltic pump 106 is coupled to the sample chamber 104 through two sections of tubing. A first section of tubing 108 couples near the sampling tube 102 to allow a sample to be pulled into the sample chamber 104. A second section of tubing 110 couples the peristaltic pump 106 to a temperature control chamber 112. The peristaltic, or tubing, pump 106 allows for a simple servicing of the pump, by replacement of tubing through the pump. For example, in some embodiments, the first section of tubing 108 and the section of tubing 110 are a single length of tubing that is threaded through the peristaltic pump 106. In other embodiments, other types of positive displacement pumps, such as piston pumps, are used. The temperature control chamber 112 includes a heatsink 114 that is thermally coupled to a Peltier block 116. The Peltier block 116 is commercially available in multiple sizes, which can be selected based on the power source, as described herein. An example of a commercially available Peltier block that can be used is part number TEC1-24108 available from EVERREDtronics of Shanghai, China. This unit does not include a heatsink. Another example of a Peltier block that can be used is the CP-110 unit from TE Technology of Traverse City, Michigan, USA. This unit includes the Peltier block and the heatsink. Peltier blocks from other manufacturers may be used.

When a sufficient amount of the hydrocarbon sample is pulled into the sample chamber 104, for example, as determined by a fluid level sensor 118, the peristaltic pump 106 shuts off. In some embodiments, the fluid level sensor 118 is an optical sensor. In other embodiments, the conductivity probe 120 is used as the level detector and the fluid level sensor 118 is omitted.

In some embodiments, after the peristaltic pump 106 shuts off, the user is prompted to close the sample chamber 104. In some embodiments, this is performed by manually closing a valve 122 on the sampling tube 102, or by removing the sampling tube 102 to allow a spring loaded flap in the valve 122 to close the sampling chamber 104. In some embodiments, the valve 122 is a solenoid operated valve that is closed automatically after the peristaltic pump 106 is shut off.

Figure 2:
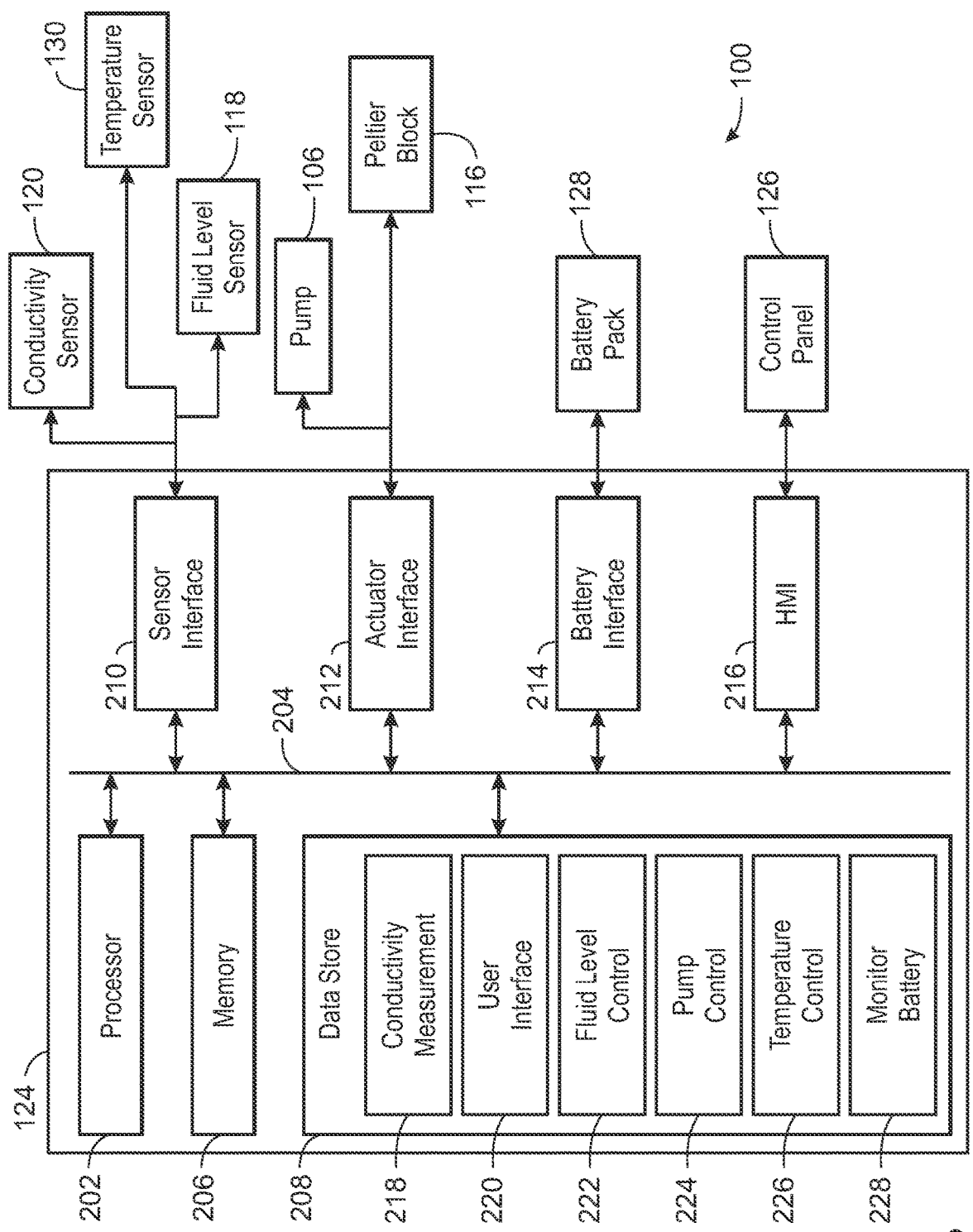
FIG. 2 is a block diagram of the smart jet fuel and diesel conductivity analyzer.

Once the sample chamber 104 is closed, a controller 124, as discussed further with respect to FIG. 2, is used to perform a conductivity measurement cycle. A control panel 126, for example, mounted on a battery pack 128, interfaces with the controller 124. A user is prompted to enter the test temperature, or setpoint, on the control panel 126.

Once the setpoint is entered, the measurement cycle is started. The peristaltic pump 106 will continuously circulate through the hydrocarbon fluid, flowing the hydrocarbon fluid over fins of the heatsink 114 attached to the Peltier block 116 from the first section of tubing 110. The heatsink 114 is heated, or cooled, by the Peltier block 116, and transfers that heat to, or from, the hydrocarbon fluid. The hydrocarbon fluid then flows over the conductivity probe 120, and is pulled back to the suction of the peristaltic pump 106. In some embodiments, the temperature is measured by a temperature sensor 130. In other embodiments, the current flow to the Peltier block 116 is used to control the temperature. The measurement cycle is continued until a stable readout of the value of the conductivity is provided. As used herein, a stable readout indicates that the value of the conductivity is changing by less than about 1%, less than about 5%, or less than about 10%.

The battery pack 128 is sized to provide the proper wattage to the Peltier block 116, in addition to powering the other operations of the analyzer 100. Controlling the sample size, for example, by using a low volume in the sample chamber 104 and controlling the size of the Peltier block 116 and battery pack 128 can be used to control the time to reach a setpoint for the temperature. In some embodiments, the battery pack 128 is removable for recharging, allowing a freshly charged battery pack to be used. In these embodiments, the controller 124 is coupled to the control panel 126 by a plug on the battery pack 128.

For example, the heating rate calculation for heating a sample from 22° C. to 35° C. in 60 seconds can be expressed as shown below:

$$Q = 2.12 \frac{kJ}{kg \cdot °C} \times 780 \frac{kg}{m^3} \times 0.03 \text{ L} \times \frac{1 \text{ m}^3}{1000 \text{ L}} \times \left( \frac{35° \text{ C.} - 22° \text{ C.}}{1 \text{ min} \times 60 \frac{s}{min}} \right)$$

$$Q = 107 \frac{J}{s} = 107 \text{ W}$$

As shown above, heating a 30 mL sample from 22° C. to 35° C. in 60 seconds requires about 107 watts of power.

This amount of power may be provided by commercially available components. For example, a 9 A, 36 VDC, Peltier block with a surface area of 40 mm² consumes about 200 watts can be powered by ten 18650-type lithium ion batteries connected in series to provide 36 VDC. For example, the batteries can be B 18650 batteries from Panasonic (3.6V 4.875 A, Lithium-Ion) of Osaka, Japan, or a single BAT838 36V 4.0 Ah battery pack from Bosch GmbH of Gerlingen-Schillerhohe, Germany. The 10 batteries would weigh about 450 grams. With a square shape of about 6.5 cm*6.5 cm, the size of the Peltier block 116 used as the heating element is fairly compact. As described above, the energy output is provided to a finned heatsink 114 constructed of an appropriate passive metal, over which the hydrocarbon fluid is passed.

The conductivity probe 120 is generally a two wire probe in which a voltage is applied between the two wires and a resistance, or voltage drop, between the wires is measured to determine conductivity. The applied voltage may be a direct current or an alternating current. The measurement as performed is compliant with ASTM D-2624.

The temperature sensor 130, if present, can be a thermocouple or a resistance temperature detector (RTD), among others. The selection of the temperature sensor can be based on the speed versus accuracy. As the temperature is quickly increasing to reach the control temperature, in some embodiments, the temperature sensor 130 is a thermocouple. In other embodiments, an RTD sensor is used as the temperature sensor 130 to obtain higher accuracy for the temperature control. However, the Peltier block 116 is a semiconductor device, generally having an accurate and reproducible calibration between applied current and the heat generated. Accordingly, in some embodiments, the temperature sensor 130 may be omitted.

The control software used in the controller 124 device may be configured so that the maximum power output to the Peltier block 116 may be used in seeking the target temperature as quickly possible. Upon temperature stabilization, the conductivity readout will appear on an integrated display on the control panel 126.

In one embodiment of the analyzer 100 as described above, the approximate dimensions of the components are follows. The battery pack 128 would weigh about 500 grams and be about 8.5 cm×3 cm×11.5 cm. The Peltier block 116 would be 6.5 cm×6.5 cm. The sample chamber 104 would be about 6.5 cm×1.5 cm×1.5 cm. The peristaltic pump 106 would be about 100 grams, with dimensions of 6 cm×5 cm×4 cm and a pumping capacity of about 100-200 mL/min. The controller 124 would be a microcontroller with dimensions of about 8 cm×8 cm×0.5 cm.

By combining the Peltier block 116 into a fluid circulation containing a conductivity probe, per ASTM D-2624, the analyzer 100 effectively resolves the issue of complex temperature interactions by targeting the fuel temperature for the conductivity measurement.

FIG. 2 is a block diagram of the smart jet fuel and diesel conductivity analyzer (the analyzer) 100. Like numbered items are as described with respect to FIG. 1.

As described herein, the analyzer 100 includes a controller 124, sensors 118, 120, and 130, actuators 106 and 116, a control panel 126, and a battery pack 128. In some embodiments, the controller 124 is capable of implementing general purpose programming languages, such as C#, Java, python, or C++, among others.

The controller 124 includes a processor 202. The processor 202 may be a microprocessor, a multi-core processor, a multithreaded processor, an ultra-low-voltage processor, or an embedded processor. In some embodiments, the processor 202 may be part of a system-on-a-chip (SoC) in which the processor 202 and the other components of the controller 202 are formed into a single integrated electronics package. In various embodiments, the processor 202 may include processors from Intel® Corporation of Santa Clara, California, from Advanced Micro Devices, Inc. (AMD) of Sunnyvale, California, or from ARM Holdings, LTD., Of Cambridge, England. Any number of other processors from other suppliers may also be used.

The processor 202 may communicate with other components of the controller 124 over a bus 204. The bus 204 may include any number of technologies, such as industry standard architecture (ISA), extended ISA (EISA), peripheral component interconnect (PCI), peripheral component interconnect extended (PCIx), PCI express (PCIe), or any number of other technologies. The bus 204 may be a proprietary bus, for example, used in an SoC based system. Other bus technologies may be used, in addition to, or instead of, the technologies above. Further, the bus 204 can include power lines from the battery pack 128 used to power the components of the analyzer 100.

The bus 204 couples the processor 202 to a memory 206. In some embodiments, such as in PLCs and other process control units, the memory 206 is integrated with a data store 208 used for long-term storage of programs and data. The memory 206 includes any number of volatile and nonvolatile memory devices, such as volatile random-access memory (RAM), static random-access memory (SRAM), flash memory, and the like. In smaller devices, such as PLCs, the memory 206 may include registers associated with the processor itself. The data store 208 is used for the persistent storage of information, such as data, applications, operating systems, and so forth. The data store 208 may be a nonvolatile RAM, a solid-state disk drive, a flash drive, or a hard disk drive, such as a micro hard disk drive, among others. In some embodiments, the data store 208 will include a flash drive.

The bus 204 couples the processor 202 to a sensor interface 210. The sensor interface 210 connects the controller 124 to the sensors used to implement the functions of the analyzer 100. In some embodiments, the sensor interface 210 is a bank of analog-to-digital converters (ADCs), an I2C bus, or a serial peripheral interface (SPI) bus, and the like. As described above, the sensors may include a fluid level sensor 118, a conductivity probe 120, and a temperature sensor 130.

The bus 204 couples the processor 202 to an actuator interface 212 used to couple the controller 124 to actuators used to operate the analyzer 100. In some embodiments, the actuator interface 212 is a bank of MOSFET power controllers, a serial peripheral interface (SPI), and the like. The actuator interface 212 couples the controller to the peristaltic pump 106 and the Peltier block 116.

The bus 204 couples the controller 124 to a battery interface 214. In some embodiments, the battery interface 214 includes lines and circuitry to couple the battery pack 128 to power lines of the bus 204. The circuitry may include monitoring circuits to track the amount of charge left in the battery pack 128, as well as fuses or other protective circuits.

The bus 204 couples the controller 124 to a human-machine interface (HMI) 216, which is used to couple the controller 124 to the control panel 126. In some embodiments, the HMI 216 is a serial bus, such as a serial peripheral interface (SPI), or a universal serial bus (USB), among others. The control panel 126 generally includes a display, such as an LCD display, for displaying measurements, and a keypad, such as a numerical keypad, for data and control entry. In some embodiments, the control panel 126 is a touch screen with programmable regions that can be configured as buttons, for example, during different operations. As described with respect to FIG. 1, the control panel 126 can be mounted on the battery pack 128. In embodiments in which the battery pack 128 is removable for charging, the coupling between the battery pack 128 and the rest of the analyzer 100 will include power and communication lines.

The data store 208 includes blocks of stored instructions that, when executed, direct the processor 202 to implement the functions of the analyzer 100. For example, the data store 208 includes a block 218 of instructions that implement the primary functions of the analyzer 100, termed conductivity measurement, although other functions are included. For example, the conductivity measurement instructions of block 218 directs the user interface to obtain the appropriate input from the user for the current point in the measurement cycle. The block 218 will also direct the fluid level control instructions of block 222 to fill the sample chamber with the hydrocarbon fluid using the pump control instructions at block 224. The block 218 will also direct the pump control instructions of block 224 and the temperature control instructions of block 226 during the conductivity measurement cycle, for example, to continuously operate the peristaltic pump 106 during the conductivity measurement cycle and direct the temperature control instructions of block 226 to power the Peltier block 116 for heating or cooling. During the conductivity measurement cycle, the conductivity measurement instructions of block 218 monitor the conductivity through the conductivity probe 120 and provide the value to the user interface of block 224 display. The conductivity measurement instructions of block 218 may also determine when the conductivity measurement is stabilized, for example, changing by less than a predetermined amount, such as 1% of the measurement value, 5% of the measurement value, 10% of the measurement value, or higher. In these embodiments, once the conductivity measurement instructions of block 218 have determined that the conductivity measurement has stabilized, an alert may be provided to user, for example, through the user interface of block 220.

The data store 208 includes the block 220 of instructions to direct the processor 202 to control user interface functions through the control panel 126. For example, the user interface will display on the control panel, at various points in the measurement, the battery status, pump controls for pulling a sample into the analyzer 100, prompts for entering temperature, controls for starting a measurement cycle, and measurement results, among others.

The data store 208 includes a block 222 of instructions for measuring and controlling the fluid level in the analyzer 100. For example, when the block 218 is directed to pull a sample into the analyzer 100, block 222 starts the peristaltic pump 106 and monitors the fluid level in the sample chamber of the analyzer 100. Monitoring the fluid level may be performed by monitoring the output from the fluid level sensor 118, or from the conductivity probe 120, or both. When the fluid level indicates that a sufficient sample has been pulled into the analyzer 100, the fluid level control of block 222 instructs the pump control of block 224 to turn off the peristaltic pump 106, and returns control to the conductivity measurement instructions of block 218.

The data store 208 includes a block 224 of instructions for controlling the pump, for example, starting and stopping the pump under the control of the conductivity measurement code of block 218 or the fluid level control of block 222.

The data store 208 includes a block 226 of instructions for controlling the temperature. The block 226 is provided the temperature set point by the conductivity measurement instructions of block 218, and activates the Peltier block 116 to control the temperature of the hydrocarbon sample. Generally this will involve heating the hydrocarbon sample using the Peltier block 116 to reach the temperature set point, although the current embodiments are not limited to heating and may use the Peltier block 116 in both a heating and cooling configurations to control the temperature at the set point. The temperature control of block 226 may also monitor the value of the temperature through the temperature sensor 130. The value of the temperature may be used for controlling the power to the Peltier block 116, and may also be provided to the user interface of block 224 display to a user. In some embodiments, the value of the temperature may be provided to the conductivity measurement of block 218 as a crosscheck on the value of the conductivity calculated.

The data store 208 may also include a block 228 of instructions to monitor the status of the battery pack 128. The instructions to monitor the battery of block 228 may be used to prevent the conductivity measurement instructions of block 218 from starting a measurement if the charge in the battery pack 128 is insufficient to complete the measurement. The instructions to monitor the battery of block 228 may also provide a battery status to the user interface of block 224 display on the control panel 126. In some embodiments, the instructions to monitor the battery of block 228 are used to provide an alert to the user interface of block 220, for example, when the charge in the battery pack 128 is insufficient to run a conductivity measurement cycle.

Figure 3:
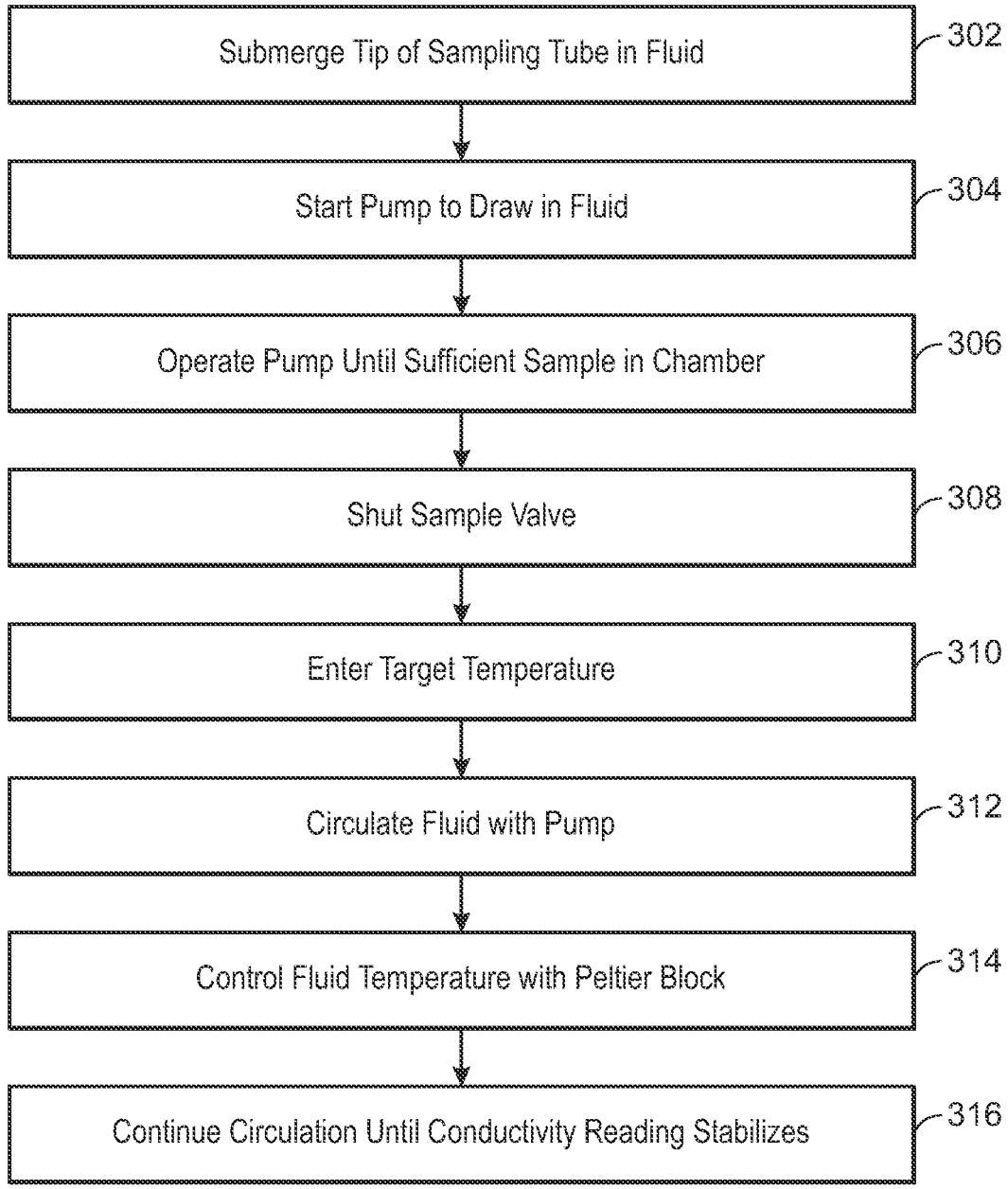
FIG. 3 is a process flow diagram of a method for using the smart jet fuel and diesel conductivity analyzer.

FIG. 3 is a process flow diagram of a method 300 for using the smart jet fuel and diesel conductivity analyzer (the analyzer). Referring also to FIG. 1, the method begins at block 302, when the tip of the sampling tube is submerged in a hydrocarbon fluid. At block 304, the pump is started to draw the hydrocarbon fluid into the analyzer. This may be performed, for example, by touching a button on the control panel after the tip of the sampling tube is submerged in the hydrocarbon fluid.

At block 306, the peristaltic pump is operated until a sufficient amount of the hydrocarbon fluid is in the sample chamber. This may be determined by monitoring a level detector in the analyzer. For example, as described herein, the analyzer may include a fluid level detector. In some embodiments, the conductivity probe is used as the level detector. Once the analyzer determines that a sufficient amount of the hydrocarbon fluid is in the sample chamber, the peristaltic pump is switched off.

At block 308, a sample valve is closed to close the sample chamber. In some embodiments, the user is prompted to close the sample chamber, for example, by shutting the sample valve or by removing the sampling tube to allow a spring-loaded valve to shut. In other embodiments, the analyzer closes the valve automatically, for example, if the sample valve is a solenoid operated valve.

At block 310, a temperature setpoint for the conductivity measurement is entered through the control panel, for example, through a prompt from the analyzer to the user. Once the temperature setpoint is entered, a measurement cycle is started.

During the measurement cycle, at block 312, the peristaltic pump is operated to continuously circulate the hydrocarbon fluid over the fins of the heat sink and the conductivity probe. At block 314, the Peltier block is powered to control the temperature of the hydrocarbon fluid. At block 316, the circulation of the hydrocarbon fluid is continued until the conductivity rating stabilizes. At that point, the user may be alerted that the reading has stabilized.

Figure 4:
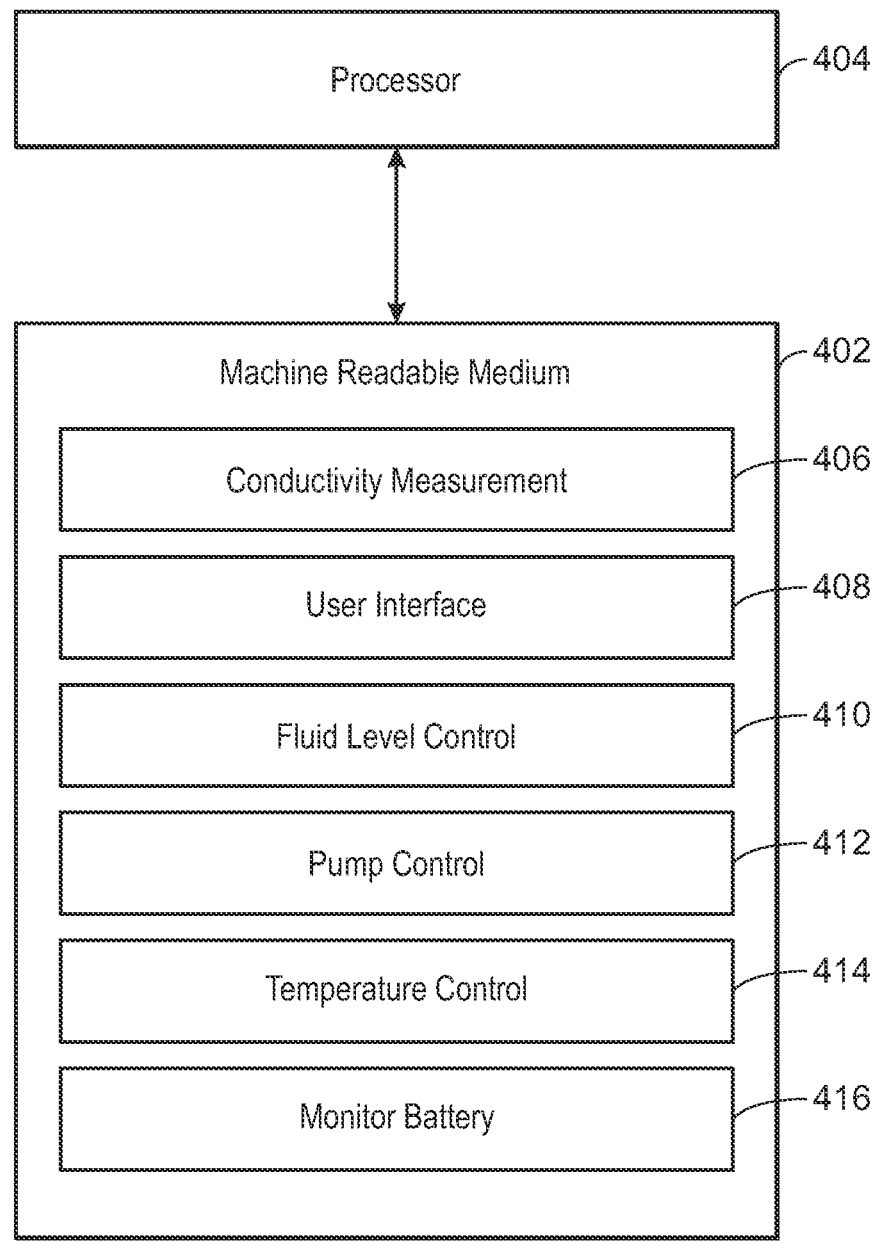
FIG. 4 is a machine-readable medium that includes code to operate a smart jet fuel and diesel conductivity analyzer.

FIG. 4 is a block diagram of a machine-readable medium 402 that includes code to operate a smart jet fuel and diesel conductivity analyzer. The machine-readable medium 402 includes instructions that, when executed by a processor 404, direct the processor 404 to implement the functions of the analyzer 100.

The machine-readable medium 402 includes instructions 406 that, when executed by the processor 404, implement the primary functions of the analyzer 100. The instructions 406 directs the processor 404 to implement instructions 408 to obtain the appropriate input from the user for the current point in the measurement cycle. The instructions 406 will also direct the processor 404 to implement instructions 410 to fill the sample chamber with the hydrocarbon fluid. The instructions 406 will also direct the processor 404 to control the pump, using instructions 412, and control the temperature, using instructions 416, during a conductivity measurement cycle. During the conductivity measurement cycle, the instructions 406 direct the processor 404 to monitor the conductivity and provide the value to a user interface using instructions 408. The instructions 406 may also direct the processor 404 to determine when the conductivity measurement is stabilized, and provide an alert to the user through instructions 408.

The machine-readable medium 402 includes instructions 408 that when executed, direct the processor 404 to perform user interface functions through a control panel. For example, the instructions 408 will direct the processor 404 to display on the control panel, at various points in the measurement, the battery status, pump controls, prompts for entering temperature, controls for starting a measurement cycle, and measurement results, among others.

The machine-readable medium 402 includes instructions 410 that, when executed, direct the processor 404 to measure and control the fluid level in the analyzer. The instructions 410, when executed, direct the processor 404 to start a peristaltic pump and monitor the fluid level in a sample chamber. The instructions 410, when executed, direct the processor 404 to turn off the pump, using instructions 412, when the fluid level indicates that is sufficient sample has been pulled into the analyzer. The machine-readable medium 402 includes instructions 412 that, when executed, direct the processor 404 to start or stop the pump.

The machine-readable medium 402 includes instructions 414 that, when executed, direct the processor 404 to control the temperature. The instructions 414, when executed, direct the processor 404 to activate the Peltier block. The instructions 414, when executed, also direct the processor 404 to monitor the temperature of the sample, or to control the current to the Peltier block to control the temperature.

The machine-readable medium 402 includes instructions 416 that, when executed, direct the processor 404 to monitor the status of a battery pack. The instructions 416, when executed, may be used to prevent the start of a conductivity measurement cycle if a measurement of the charge in the battery pack 128 is insufficient to complete the conductivity measurement cycle. The instructions 416, when executed, may also provide a battery status to a user through the control panel.

Embodiments

An embodiment described in examples herein provides a conductivity analyzer for hydrocarbons. The conductivity analyzer includes a peristaltic pump to flow the hydrocarbons over a temperature controller and a conductivity probe.

The temperature controller includes a Peltier block. The conductivity analyzer also includes the conductivity probe.

In an aspect, the conductivity analyzer includes a battery pack including sufficient power to allow the conductivity analyzer to be portable. In an aspect, the conductivity analyzer includes a sampling tube to sample a hydrocarbon fluid.

In an aspect, the conductivity analyzer includes a fluid level sensor to determine when a sample chamber is full.

In an aspect, the conductivity analyzer includes a valve to close off the sample chamber. In an aspect, the valve includes a spring-loaded flap that closes when a flexible sample tube is removed. In an aspect, the conductivity analyzer the valve includes a solenoid valve.

In an aspect, the conductivity analyzer includes a control panel for entry of setpoints and display of data. In an aspect, the conductivity analyzer includes a temperature sensor.

In an aspect, the conductivity analyzer includes a controller. The controller includes a processor, a human-machine interface (HMI) coupled to a control panel, a sensor interface coupled to sensors. The sensors including the conductivity probe and a temperature sensor. The controller includes an actuator interface coupled to actuators. The actuators including the Peltier block and the peristaltic pump. The controller also includes a data store, wherein the data store includes code to direct the processor to obtain a temperature setpoint through the control panel, activate the peristaltic pump, control the Peltier block to adjust a temperature of the hydrocarbons to the setpoint, and measure the conductivity of the hydrocarbons while the temperature is adjusted.

In an aspect, the conductivity analyzer includes a rechargeable battery pack. In an aspect, the rechargeable battery pack includes a control panel. In an aspect, the rechargeable battery pack is removable for charging.

Another embodiment described in examples herein provides a method for using a conductivity analyzer for hydrocarbons. The method includes operating a peristaltic pump to circulate hydrocarbons over a heatsink coupled to a Peltier block and over a conductivity probe, adjusting a temperature of the hydrocarbons to a temperature setpoint, and measuring a conductivity of the hydrocarbons while adjusting the temperature.

In an aspect, the method includes operating the peristaltic pump until the conductivity reading stabilizes.

In an aspect, the method includes immersing a tip of a sampling tube into the hydrocarbons, operating the peristaltic pump to pull a sample of hydrocarbons into the sample chamber in the conductivity analyzer, and closing the sample chamber.

In an aspect, the method includes closing a valve on the sampling tube to close the sample chamber. In an aspect, the method includes removing the sampling tube to close the sample chamber.

In an aspect, the method includes entering the temperature setpoint through a control panel on the conductivity analyzer.

Another embodiment described in examples herein provides a machine-readable medium. The machine-readable medium includes instructions that, when executed by a processor direct the processor to perform a conductivity measurement cycle on a hydrocarbon fluid using an analyzer.

In an aspect, the machine-readable includes instructions that, when executed by the processor, direct the processor to obtain set points or provide data to a control panel.

In an aspect, the machine-readable medium includes instructions that, when executed by the processor, direct the processor to pull a sample of fluid into the analyzer.

In an aspect, the machine-readable medium includes instructions that, when executed by the processor, direct the processor to turn a pump on or off.

In an aspect, the machine-readable medium includes instructions that, when executed by the processor, direct the processor to activate a Peltier block to control a temperature of the hydrocarbon fluid.

In an aspect, the machine-readable medium includes instructions that, when executed by the processor, direct the processor to monitor the status of a battery pack.

Other implementations are also within the scope of the following claims.

What is claimed is:

1. A conductivity analyzer for hydrocarbons, comprising:
   a peristaltic pump to flow the hydrocarbons over a temperature controller and a conductivity probe;
   a sample chamber comprising the conductivity probe;
   a fluid level sensor;
   the temperature controller comprising a Peltier block;
   the conductivity probe; and
   a controller, comprising:
     a processor;
     a human-machine interface (HMI) coupled to a control panel;
     a sensor interface coupled to sensors comprising:
       the conductivity probe; and
       a temperature sensor;
     an actuator interface coupled to actuators comprising:
       the Peltier block; and
       the peristaltic pump; and
     a data store, wherein the data store comprises code to direct the processor to turn off the peristaltic pump when the fluid level sensor indicates that the sample chamber is filled with a predetermined amount of the hydrocarbons.

2. The conductivity analyzer of claim 1, comprising a battery pack comprising sufficient power to allow the conductivity analyzer to be portable.

3. The conductivity analyzer of claim 1, comprising a sampling tube to sample a hydrocarbon fluid.

4. The conductivity analyzer of claim 1, comprising a valve to close off the sample chamber.

5. The conductivity analyzer of claim 4, wherein the valve comprises a spring-loaded flap that closes when a flexible sample tube is removed.

6. The conductivity analyzer of claim 4, wherein the valve comprises a solenoid valve.

7. The conductivity analyzer of claim 1, comprising a control panel for entry of setpoints and display of data.

8. The conductivity analyzer of claim 1, comprising a temperature sensor.

9. The conductivity analyzer of claim 1, wherein the data store comprises code to direct the processor to:
   obtain a temperature setpoint through the control panel;
   activate the peristaltic pump;
   control the Peltier block to adjust a temperature of the hydrocarbons to the setpoint; and
   measure the conductivity of the hydrocarbons while the temperature is adjusted.

10. The conductivity analyzer of claim 1, comprising a rechargeable battery pack.

11. The conductivity analyzer of claim 10, wherein the rechargeable battery pack comprises a control panel.

12. The conductivity analyzer of claim 10, wherein the rechargeable battery pack is removable for charging.

13. The conductivity analyzer of claim 1, wherein the data store comprises code to direct the processor to close the sample chamber when the fluid level sensor indicates that the sample chamber is filled with a predetermined amount of the hydrocarbons.

14. The conductivity analyzer of claim 1, wherein the data store comprises code to direct the processor to turn on the peristaltic pump to circulate the hydrocarbons in the conductivity analyzer.

15. A method for using a conductivity analyzer for hydrocarbons, comprising:
operating a peristaltic pump to circulate hydrocarbons over a heatsink coupled to a Peltier block and over a conductivity probe;
adjusting a temperature of the hydrocarbons to a temperature setpoint; and
measuring a conductivity of the hydrocarbons while adjusting the temperature.

16. The method of claim 15, comprising operating the peristaltic pump until the conductivity reading stabilizes.

17. The method of claim 15, comprising:
immersing a tip of a sampling tube into the hydrocarbons;
operating the peristaltic pump to pull a sample of hydrocarbons into the sample chamber in the conductivity analyzer; and
closing the sample chamber.

18. The method of claim 17, comprising closing a valve on the sampling tube to close the sample chamber.

19. The method of claim 17, comprising removing the sampling tube to close the sample chamber.

20. The method of claim 15, comprising entering the temperature setpoint through a control panel on the conductivity analyzer.

21. A machine-readable medium comprising instructions that, when executed by a processor direct the processor to activate a Peltier block to control a temperature of the sample;
collect a sample of a hydrocarbon fluid using a peristaltic pump;
circulate the sample using the peristaltic pump over an analyzer; and perform a conductivity measurement cycle on the sample using the analyzer.

22. The machine-readable medium of claim 21, comprising instructions that, when executed by the processor, direct the processor to obtain set points or provide data to a control panel.

23. The machine-readable medium of claim 21, comprising instructions that, when executed by the processor, direct the processor to turn a pump on or off.

24. The machine-readable medium of claim 21, comprising instructions that, when executed by the processor, direct the processor to monitor the status of a battery pack.

* * * * *